United States Patent [19]
Kirkpatrick

[11] Patent Number: 5,773,259
[45] Date of Patent: Jun. 30, 1998

[54] TISSUE REMODELING PROTEINS

[75] Inventor: Robert B. Kirkpatrick, King of Prussia, Pa.

[73] Assignee: SmithKline Beecham Corporation, Philadelphia, Pa.

[21] Appl. No.: 815,990

[22] Filed: Mar. 10, 1997

Related U.S. Application Data

[60] Provisional application No. 60/013,746, Mar. 20, 1996.

[51] Int. Cl.$^6$ .......................... C12P 19/34; G01N 33/53; C07H 21/02; C07H 21/04
[52] U.S. Cl. ...................... 435/91.2; 435/91.1; 436/500; 530/398.1; 536/22.1
[58] Field of Search ................................. 435/91.2, 91.1; 436/500; 530/398.1; 536/22.1, 24.3

[56] References Cited

U.S. PATENT DOCUMENTS 4,965,188  10/1990  Mullis et al. ................................ 435/6

FOREIGN PATENT DOCUMENTS

WO 95/01995  1/1995  WIPO ............................ C07K 15/00
WO 95/02188  1/1995  WIPO .......................... G01N 33/574

OTHER PUBLICATIONS

Nyirkos, Peter & Golds, E.E.; *Human synovial cells secrete a 39 kDa protein similar to a bovine mammary protein expressed during thr non–lactating period;* Biochemistry (1990); vol. 269; pp. 265–268.

Johansen, J.S., Jensen, H.S. Price, P.A.; *A New Biochemical Marker for Joint Injury. Analysis of YKL–40 in Serum and Synovial Fluid;* British Journal for Rhematology 1993; vol. 32; No. 11; pp. 949–955.

Rejman, J.J., Hurley, W.L.; *Isolation and Characterization of a Novel 39 Kilodalton Whey Protein from Bovine Mammary Secretions Collected During the Nonlactating Period;* Biochemical and Biophysical Research Communications; Jan. 15, 1988; vol. 150, No. 1; pp. 329–334.

Kirkpatrick, Robert B., Matico, R.E., McNulty, D.E., Strickler, J.E., Rosenberg, M.; *An abundantly secreted glycoprotein from Drosophila melanogaster is related to mammalian secretory proteins produced in rheumatoid tissues and by activated macrophages;* Gene 153 (1995); pp. 147–154.

Johansen, J.S., Cintin, C., Jorgensen, M., Kamby, C., Price, P.A.; *Serum YKL–40: a New Potential Marker of Prognisis and Location of Metastases of Patients with Recurrent Breast Cancer;* European Journal of Cancer; 1995; vol. 31A; No. 9; pp. 1437–1442.

Johansen, J.S., Williamson. M.K., Rice, J.S., Price P.A.; *Identification of Proteins Secreted by Human Osteoblastic Cells in Culture;* Journal of Bone and Mineral Research; vol. 7; No. 5; 1992; pp. 501–512.

Shackelton, L. M., Mann, D.M., Millis, Albert J.T.;*Identification of a 38–kDa Heparin–binding Glycoprotein (gp38k) in Differentiating Vascular Smooth Muscle Cells as a Member of a Group of Proteins Associated with Tissue Remodeling;* Journal of Biochemistry; vol. 270; No. 22; Issue of Jun. 2, 1995; pp. 13076–13083.

Hakala et al. Human cartilage gp–39, a major secretory product of articular chondrocytes and synovial cells, is a mammalian memeber of a chitinase protein family, J. Biol. Chem. vol. 268(4), pp. 25803–25810, 1993.

Primary Examiner—Kenneth R. Horlick
Assistant Examiner—Joyce Tung
Attorney, Agent, or Firm—William T. Han; William T. King; Edward T. Lentz

[57] ABSTRACT

The invention relates to a method of diagnosing artherosclerosis by detecting mutation or altered expression of HC gp-39.

1 Claim, No Drawings

TISSUE REMODELING PROTEINS

This application claims the benefit of U.S. provisional Application No. 60/013,746 filed Mar. 20, 1996.

BACKGROUND OF THE INVENTION

The generation or destruction of tissue requires constant reorganization and restructuring of the extracellular matrix (ECM) components including interstitial collagens, basement membrane collagen, fibronectin, laminin, aggrecan, and various proteoglycans. Heinegard and Oldberg, *FASEB J.* 1989, 3, 2042–2051; Woessner *FASEB J.* 1991, 5, 214–2154. Normal types of remodeling processes include embryonic development, post-partum involution of the uterus, ovulation, wound healing, and bone and growth plate remodeling. Woessner et al. *Steroids* 1989, 54, 491–499; Weeks et al. *Biochim Biophys Acta* 1976, 445, 205–214; Lepage and Gache *EMBO J.* 1990, 9, 3003–3012; Wride and Sanders *Dev-Dyn.* 1993, 198(3) 225–39. Similar processes also occur in disease states such as joint destruction in rheumatoid and osteoarthritis, periodontia and tumor cell metastasis. Thompson and Oegema *J Bone Joint Surg.* 1979, 61, 407–16; Reynolds et al. *Adv-Dent-Res.* 1994, 8(2) 312–9. One example of these processes is the migration of macrophages to the site of inflammation as in the case of synovial tissue in rheumatoid arthritis. Cutolo et al. *Clin. and Exper. Rheum.* 1993, 11, 331–339. The ECM components are regulated, in both normal and disease states, by various exogenous and endogenous factors. For example, in tumor formation, the differentiation state of the cell can increase the rate of degradation of the ECM. Benya *Pathol. Immunopathol. Res.* 1988, 7, 51–54. Likewise, the presence of metalloproteinases or their inhibitors can alter the composition of the ECM. An imbalance of metalloproteinases and tissue inhibitors of matrix metalloproteinases (TIMP) has been shown to contribute to the pathogenesis of osteoarthritis. Dean et al. *J. Clin. Invest.* 1989, 84: 678–685. Cytokines, growth factors, and the extracellular environment can all contribute to the alteration of the ECM. Tyler *Biochem J.* 1985, 227, 869–878; Dinarello *Sem Immunol.* 1992, 4, 133–145; McConnell et al. *J. Cell Biol.* 1987, 105, 1087–98.

The growth of cartilage and bone is actualized by cells such as articular chondrocytes and osteoblasts. The main function of these cells in immature tissue is the deposition and remodeling of the cartilage or bone matrix. In adult tissue, these cells maintain this matrix in order to ensure its proper function. In both cases, this encompasses secretion of the extracellular components as well as secretion of proteins involved in the turnover of the ECM.

A major species of protein secreted by these cells and involved in the turnover of the ECM are the metalloproteinases. Woessner *FASEB J.* 1991, 5, 214–2154. A new type of secretory glycoprotein has also been identified in human cartilage, osteoblasts, synovial cells, sheep and bovine oviduct and mammary cells, and macrophages. Nyrikos and Golds *Biochem J.* 1990, 268, 265–268; Hakala et al. *J. Biol. Chem.* 1993, 268(34) 25803–25810; Johansen et al. *J. Bone and Min. Res.* 1992, 7(5) 501–511; Rejman and Hurley *Biochem. Biophys. Res. Commun.* 1988, 150, 329–334; DeSouza and Murray *Endocrinology* 1995, 136(6) 2485–2496; Hollak et al. *J. Clin. Invest.* 1994, 93, 1288–92; Arias et al. *Biol. of Reproduction* 1994, 51, 685–694. These novel mammalian proteins all share regions of significant homology to the bacterial and fungal chitinases and, therefore, are referred to herein as "chitinase-like" proteins.

Chitinases are enzymes that hydrolyze glycosidic bonds. They bear a subtle similarity to lysozymes from mammals and function as endoglycosidases with a specificity for N-acetyl-glucosamine linkages. However, these types of chitin-like structures, homopolymers of N-acetyl-glucosamine, are not normally encountered in mammalian tissue.

The human cartilage glycoprotein, HC gp-39, is a protein with an apparent molecular weight of approximately 39 kDa secreted by both articular chondrocytes and synovial fibroblasts. Nyrikos and Golds *Biochem J.* 1990, 268, 265–268; Hakala et al. *J. Biol. Chem.* 1993, 268(34), 25803–25810. This protein has been described as a marker for joint injury, appearing in the blood and synovial fluid from patients diagnoses with rheumatoid arthritis. Johansen et al. *British J. of Rheumatology* 1993, 32, 949–955. The gene encoding this protein has been cloned and is expressed specifically in cartilage and synovial cells of rheumatic joints. Hakala et al. *J. Biol. Chem.* 1993, 268(34), 25803–25810. The protein YKL-40 has also been identified as one of the major secretory products of cultured human osteoblastic cells (osteocarcinoma cell line MG-63) expressed in response to 1,25-dihydroxyvitamin D3 stimulation. Johansen et al. *J. Bone and Min. Res.* 1992, 7(5), 501–511; Johansen et al. *Br. J. Rheumatol.* 1993, 32, 949–55. The N-terminal portion of YKL-40 was sequenced and found to be identical to HC gp-39. Upon further sequencing, YKL-40 and HC gp-39 were found to be identical.

As provided herein, chitinase-like polypeptides, including, for example, HC gp-39 are believed to be involved in tissue remodeling in the mammalian cell and thus serve as a useful tool in the development of therapeutics and diagnostics for tissue remodeling disorders.

SUMMARY OF THE INVENTION

In accordance with one aspect of the present invention, there is provided a process for utilizing a chitinase-like polypeptide, particularly HC gp-39 polypeptide, for therapeutic purposes, for example, in the treatment of tissue remodeling disorders.

In accordance with a further aspect of the present invention, there is provided a process for utilizing a chitinase-like polypeptide, particularly HC gp-39 polypeptide, for diagnostic purposes, for example, in the diagnosis of tissue remodeling disorders.

In accordance with a further aspect of the present invention, there is provided a monoclonal antibody against HC gp-39, particularly against recombinant HC gp-39 (rHC gp-39).

These and other aspects of the present invention should be apparent to those skilled in the art from the teachings herein.

DETAILED DESCRIPTION OF THE INVENTION

It is now believed that the chitinase-like proteins, especially, for example, HC gp-39 are involved in tissue remodeling. HC gp-39 is homologous to microbial chitinases. In particular these proteins share a similar cysteine motif and homology to the active site of microbial chitinases. Accordingly, these proteins can be used in the development of treatments for tissue remodeling diseases and in the diagnosis of these diseases.

A number of experiments were performed which point to the role of HC gp-39 as a product of macrophages. Primary human monocytes, activated to become macrophages through adherence to plastic, secrete high levels of HC gp-39 into the culture media. In addition, the induction of HC gp-39 expression has been correlated with the differentiation of myeloid cell lines HL60 and U937 toward a macrophage lineage by induction with phorbol ester. HC gp-39 message can be detected in human atherosclerotic plaques derived from endarterectomies. Accordingly, it is believed that chitinases and, in particular, HC gp-39 function in various tissues undergoing extensive remodeling, such as, for example, myeloid and macrophage cells, including those cells associated with rheumatoid arthritis and atherosclerosis where macrophages play an important role. Further, rHC gp-39 was shown to stimulate in vitro smooth muscle cell migration, indicative of involvement in the remodeling processes occurring in diseases arteries.

Chitinase-like proteins can also be used in the production of antibodies. The proteins, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against these proteins can be obtained by direct injection of the protein into an animal, preferably a nonhuman. The antibody so obtained will then bind the protein itself. In this manner, even a sequence encoding only a fragment of the protein can be used to generate antibodies binding the whole native protein. Such antibodies can then be used to isolate these proteins from tissue expressing these proteins.

For preparation of monoclonal antibodies, any technique which provides antibodies produced by continuous cell line cultures can be used. Examples include the hybridoma technique (Kohler and Milstein *Nature* 1975, 256, 495–497), the trioma technique, the human B-cell hybridoma technique (Kozbor et al. *Immunology Today* 1983, 4, 72), and the EBV-hybridoma technique to produce human monoclonal antibodies (Cole et al. in *Monoclonal Antibodies and Cancer Therapy*, Alan R. Liss, Inc., 1985, pp. 77–96).

A preferred monoclonal antibody is provided by the invention, made against, and capable of recognizing HC gp-39. A more preferred antibody recognizes rHC gp-39. Such monoclonal antibodies can neutralize the activity of HC gp-39, including but not limited to rHC gp-39 and/or can immunoprecipitate HC gp-39 and rHC gp-39. It is preferred that the antibodies are used at a concentration of between about 0.01 mg/ml and 1 mg/ml, particularly between about 0.1 mg/ml and 0.5 mg/ml, and more particularly between about 0.25 mg/ml and 0.35 mg/ml.

Techniques described for the production of single chain antibodies (U.S. Pat. No. 4,946,778) can be adapted to produce single chain antibodies to immunogenic chitinase-like protein product. Also, transgenic mice may be used to express humanized antibodies to immunogenic chitinase-like protein products.

This invention is also related to the use of these chitinase-like protein as a diagnostic. Detection of a mutated form of HC gp-39 will allow a diagnosis of a tissue remodeling disease such as rheumatoid arthritis or artherosclerosis.

Individuals carrying mutations in one or more of these chitinase-like proteins may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature* 1986, 324, 163–166) prior to analysis. RNA or cDNA may also be used for the same purpose. As an example, PCR primers complementary to the nucleic acid encoding HC gp-39 can be used to identify and analyze mutations in this protein. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded temperature molecular generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamidine gradient gels in which the mobilities of different DNA fragments are retarded in the gel at different positions according to their specific melting or partial melting temperatures (see, e.g., Myers et al. *Science* 1985, 230, 1242). Sequence changes at specific locations may also be revealed by nuclease protection assays, such as RNase and S1 protection or the chemical cleavage method (e.g., Cotton et al. *PNAS USA* 1985, 85, 4397–4401.

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of chitinase-like proteins in various tissues. Assays used to detect levels of these proteins in a sample derived from a host are well-known to those of skill in the art and include radioimmunoassays, competitive-binding assays, Western Blot analysis and preferably an ELISA assay. An ELISA assay initially comprises preparing an antibody specific to a chitinase-like protein, preferably a monoclonal antibody. In addition, a reporter antibody is prepared against the monoclonal antibody. To the reporter antibody is attached a detectable reagent such as radioactivity, fluorescence or in this example a horseradish peroxidase enzyme. A sample is removed from a host and incubated on a solid support, e.g., a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any chitinase-like proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to the chitinase-like protein. Unattached reporter antibody is then washed out. Peroxidase substrates are then added to the dish and the amount of color developed in a given time period is a measurement of the amount of chitinase-like protein present in a given volume of patient sample when compared against a standard curve.

A competition assay may be employed wherein antibodies specific to the chitinase-like protein are attached to a solid support and labeled protein and a sample derived from the host are passed over the solid support and the amount of label detected attached to the solid support can be correlated to a quantity of chitinase-like protein in the sample.

The following examples are provided for illustrative purposes only and are not intended to limit the invention.

EXAMPLES

Example 1

Expression of HC gp-39 in vitro

Recombinant HC gp-39 was produced in vitro by transfecting an expression vector (CDN) containing the cDNA into CHO cells and selecting stable cell lines.

The full length HC gp-39 gene was cloned into CDN in two pieces; a 660 bp Sac II-Bst EII fragment plus a 678 bp Bst EII-Bcl fragment, ligated together with the CDN vector cut with Sac II-Bcl I. This construct was transfected into CHO ACC 317 cells by standard methods. Specifically, 20 mg of the HC gp-39 plasmid construct was linearized by restriction digestion and electroporated into $1.25 \times 10^7$ cell in 1 ml. Cells were seeded at a density of $2.5 \times 10^3$ cells per well and selected in minimal media in the absence of nucleosides. Secreted protein was recovered from the conditioned media and purified using Q sepharose flow through, S sepharose capture and sized on Suprose 12. The resulting material was greater than 95% pure as determined by Coomassie blue staining.

Example 2

Assay for Smooth Muscle Migration

Smooth muscle migration was measured in a chamber divided by a semi-permeable filter to which rHC gp-39 2.3 µg/ml) was bound on one side. On the other side, human fetal smooth muscle cells were cultured. The extent to which cells migrated into the filter was monitored colorimetrically (optical density). rHC gp-39 elicited a stronger migration response in this assay than PDGF, a known stimulator of smooth muscle migration.

Example 3

Production and Characterization of Antibodies Generated Against HC gp-39

Murine monoclonal antibodies were produced using purified rHC gp-39. Purified rHC gp-39 was used as the immunogen for a panel of seven female mice (Charles Rive, Wilmington, Mass.). The animals received three subcutaneous injections of rHC gp-39 in phosphate buffered saline (PBS) emulsified with a one to one ratio of TiterMAX® (CytoRx Corp., Norcross) over a period of four months. The priming antigen dose was 50 mg and boosts were 25 mg and 10 mg. After boosts, serum samples were collected and assayed for binding to rHC gp-39. Animals producing serum samples that bound rHC gp-39 were selected as spleen donors and boosted intravenously with 10 mg rHC gp-39 prior to euthanasia.

The fusion procedure, first reported by Kohler et al. (*Nature* 1975, 256, 495) was used with modifications to perform the technique using a cell monolayer (Kennet et al. Eds., "*Hybridomas: A new dimension in biological analysis*", pp. 368–377, Plenum Press, New York). Spleen cells from two donor mice were pooled and fusions performed using a ratio of 50 million spleen cells to ten million SP2/0/Ag14 myeloma cells. Supernatants from fusion-positive wells were assayed by binding to rHC gp-39 by ELISA.

Monoclonal antibodies (2G10, 5C11, 11C4, 17D12, 18B3, 11H4, and 5C12) were characterized for their ability to immunoprecipitate HC gp-39 with protein A sepharose. In addition, these monoclonal antibodies have been tested for their ability to neutralize binding of HC gp-39 to sites found in lung tissue. Several of these mAbs both immunoprecipitate and neutralize binding activity (mAbs 2G10, 5C12, 18B3, 11H4, 11C4, 17D12, 5C11 over a range from 0.01 mg/ml to 1 mg/ml).

What is claimed is:

1. A method of diagnosing atherosclerosis by detecting a mutation in chitinase-like protein HC gp-39 in a host comprising:

(a) synthesizing PCR primers complementary to a nucleic acid encoding a normal chitinase-like protein HC gp-39;

(b) obtaining nucleic acids from cells of a host;

(c) amplifying the obtained nucleic acids with the synthesized PCR primers to obtain an amplified product;

(d) comparing the amplified product to a normal genotype encoding the normal chitinase-like protein HC gp-39 to detect any mutations in the amplified product (e) and correlating any mutations with the presence of atherosclerosis.

\* \* \* \* \*